United States Patent
Melilli

(10) Patent No.: US 11,751,862 B2
(45) Date of Patent: Sep. 12, 2023

(54) MULTIFUNCTION QUICK CONNECT SOCKET FOR SURGICAL RETRACTION TOOLS

(71) Applicant: TERUMO CARDIOVASCULAR SYSTEMS CORPORATION, Ann Arbor, MI (US)

(72) Inventor: Bryan Melilli, North East, MD (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 488 days.

(21) Appl. No.: 17/141,493

(22) Filed: Jan. 5, 2021

(65) Prior Publication Data

US 2021/0121167 A1    Apr. 29, 2021

Related U.S. Application Data

(63) Continuation-in-part of application No. 16/600,810, filed on Oct. 14, 2019, now Pat. No. 11,317,899.

(51) Int. Cl.
*A61B 17/02* (2006.01)
(52) U.S. Cl.
CPC .. *A61B 17/0206* (2013.01); *A61B 2017/0237* (2013.01); *A61B 2017/0287* (2013.01)
(58) Field of Classification Search
CPC ................................ A61B 17/0206; A61B 2017/00477–2017/00486
See application file for complete search history.

(56) References Cited

U.S. PATENT DOCUMENTS

| 4,457,300 A | 7/1984 | Budde |
| 6,338,738 B1 * | 1/2002 | Bellotti ................. F16M 11/40 606/232 |
| 6,551,242 B1 * | 4/2003 | Furnish .............. A61B 17/0206 600/235 |

(Continued)

FOREIGN PATENT DOCUMENTS

WO    2004052178 A2    6/2004

OTHER PUBLICATIONS

Assistant™ Attachments with StableSoft™ Technology, Terumo Product Brochure, Jan. 2018.

(Continued)

*Primary Examiner* — Zade Coley
(74) *Attorney, Agent, or Firm* — MacMillan, Sobanski & Todd, LLC

(57) ABSTRACT

A surgical stabilizer arm ends with a hybrid quick connect mechanism capable of holding tissue manipulator tools of either the ball type or the shaft type. The single integrated mechanism allows users to choose the type of attachment mechanism they prefer on a case-by-case basis. The mechanism has a spring-loaded sleeve that can be pulled back to enable an attachment (manipulator tool) to be inserted. A ball-style attachment is inserted through an opening in a grip cage, and a shaft-style attachment is inserted into an actuator (e.g., spring detent) through the claws of the grip cage. When the sleeve is released, a compression spring pushed the actuator forward, either pressing the ball attachment against the grip cage or pressing the spring detent against the shaft attachment to partially lock the attachment in place. Tightening a tension cable increases the pressure to fully lock the attachment in place.

20 Claims, 14 Drawing Sheets

(56) References Cited

U.S. PATENT DOCUMENTS

| | | | |
|---|---|---|---|
| 6,652,454 B2 * | 11/2003 | Hu | A61B 17/0206 |
| | | | 600/232 |
| 6,656,113 B2 | 12/2003 | Green, II et al. | |
| 7,018,328 B2 | 3/2006 | Mager et al. | |
| 7,226,448 B2 | 6/2007 | Bertolero et al. | |
| 7,585,277 B2 | 9/2009 | Taylor et al. | |
| 7,682,305 B2 | 3/2010 | Bertolero et al. | |
| 7,749,157 B2 | 7/2010 | Bertolero | |
| 9,498,198 B2 | 11/2016 | Hu et al. | |
| 2002/0177753 A1 * | 11/2002 | Dobrovolny | A61B 17/02 |
| | | | 600/234 |

OTHER PUBLICATIONS

Beating Heart and Surgical Stabilization Product Portfolio, Terumo Product Brochure, Jul. 2015.

* cited by examiner

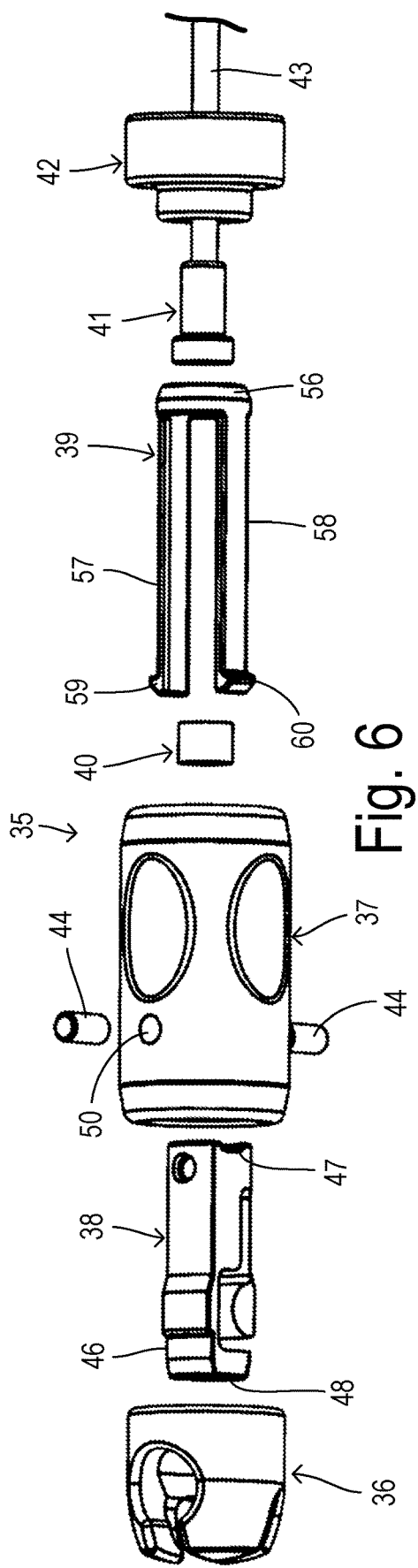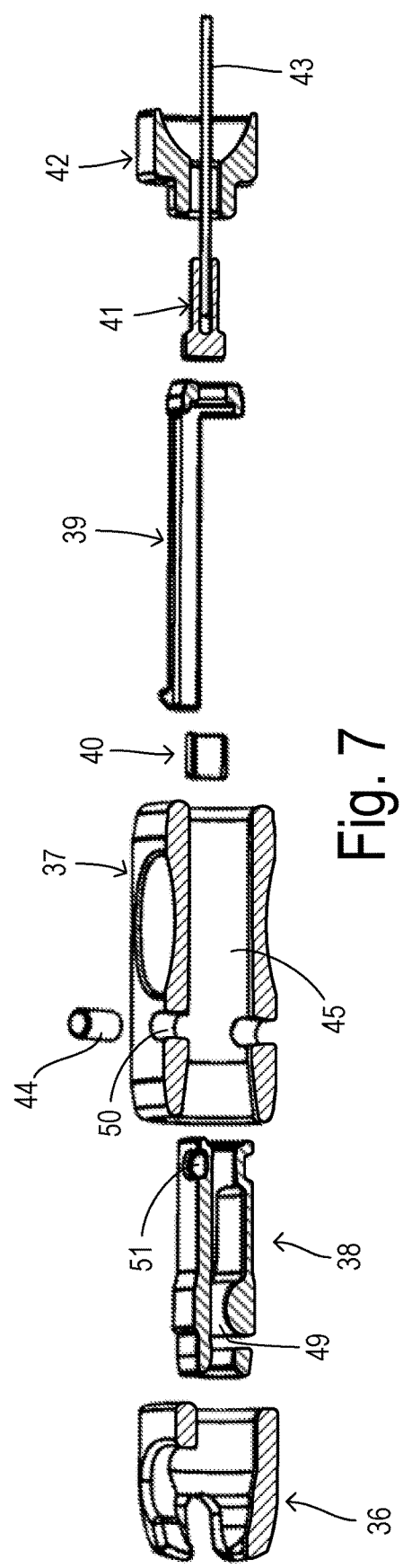

MULTIFUNCTION QUICK CONNECT SOCKET FOR SURGICAL RETRACTION TOOLS

CROSS REFERENCE TO RELATED APPLICATIONS

This application is a continuation-in-part of co-pending U.S. application Ser. No. 16/600,810, filed Oct. 14, 2019, entitled "Ball-To-Shaft Quick Connect Adapter For Surgical Retraction Tools," which is incorporated herein by reference.

STATEMENT REGARDING FEDERALLY SPONSORED RESEARCH

Not Applicable.

BACKGROUND OF THE INVENTION

The present invention relates in general to tissue retractors and stabilizers used for surgical procedures, and, more specifically, to the attachment of retractor/stabilizer tools to the end of a stabilizer arm.

Many different types of surgical procedures are facilitated by mechanical devices to retract, restrain, or otherwise situate tissues and other body structures in and around a surgical site. During cardiac surgery, for example, a sternal retractor is typically mounted over the patient having spaced retractor blades on a frame wherein the blades are inserted into an incision and spread apart for separating the tissues overlying the surgical site. The frame of the sternal retractor has also been used to support additional "rakes" (i.e., retractors) and other fixed tools or devices in order to manipulate organs or tissues within the larger surgical field, as shown in U.S. Pat. No. 5,772,583, for example.

For obtaining compact and strong placement of such tools while avoiding complicated position adjustment mechanisms, a stabilizer arm has been employed having a bendable shaft that is anchored to a fixed frame and having a quick-connect mechanism at its distal end for receiving various attachments (i.e., tools, rakes, suction stabilizers, positioners, and other instruments). The attachments are collectively referred to herein as tissue manipulator tools.

One example of a commercially-available stabilizer arm is the Hercules™ Stabilizing Arm, sold by Terumo Cardiovascular Systems Corporation of Ann Arbor, Mich. This stabilizer arm includes a lockable, articulating column wherein a central tensioning cable is strung through a series of links. When the cable is tensioned (e.g., by rotating a handle), the links move toward each other to interlock via a series of ball and socket joints. The column becomes rigid when the central cable is tensioned. Releasing the tension (e.g., by counter-rotating the handle) returns the column to the flexible state. In the relaxed state, enough tension may be maintained to weakly remain in position as the column is adjusted to a desired configuration. The ball and socket joints are generally hemispherical so that side-to-side adjustment angles are available over a wide range. The stabilizer arm may be reusable for many procedures after being properly sterilized. The quick-connect mechanism at the distal end of the articulating column receives compatible tools that may be either disposable or reusable.

Various types of mechanisms have been adopted for the quick-connect function, including ball-type and shaft-type. For the ball-type, the tool includes a mounting shaft ending in a ball shape that is retained in a collet on the distal end of the stabilizer arm. In an unclamped state, arms of the collet are movable to allow the ball shape to be snapped into the collet. In a clamped state, the collet arms are compressed against the ball to rigidly hold the tool. For the shaft type, the tool ends with a straight shaft which is inserted into an axial bore on the distal end of the stabilizer arm. The shaft is held in the bore by a movable latch or pin in the stabilizer arm that selectably presses against the shaft. The shaft may have an indent or catch on one side to engage the latch.

A typical surgical facility or room may have stabilizer arms available which all employ just one of the types of quick-connect mechanisms. Since tools must be compatible with the quick-connect mechanism, any particular tool can be used only with a particular type of stabilizer arm. Thus, when only one particular type of stabilizer arm is available to a user, only the tools compatible with that particular type can be used. It would be desirable to enable certain tools made for one type of quick connect to be used (i.e., mounted to) a stabilizer arm having a different type of quick connect.

SUMMARY OF THE INVENTION

The invention provides a hybrid quick connect mechanism capable of holding tissue manipulator tools of either the ball type or the shaft type. The single integrated mechanism allows users to choose the type of attachment mechanism they prefer on a case-by-case basis. The mechanism has a spring-loaded sleeve that can be pulled back to enable an attachment (manipulator tool) to be inserted. A ball-style attachment is inserted through an opening in a grip cage, and a shaft-style attachment is inserted into an actuator (e.g., spring detent) through the claws of the grip cage. When the sleeve is released, a compression spring pushed the actuator forward, either pressing the ball attachment against the grip cage or pressing the spring detent against the shaft attachment to partially lock the attachment in place. Tightening a tension cable increases the pressure to fully lock the attachment in place.

In one aspect of the invention, a surgical stabilizer arm is configurable to retain tissue manipulator tools with either a shaft end or a ball end. The stabilizer comprises a cylindrical sleeve with a central cavity. A dual actuator is provided having a proximal end fixed in the central cavity and a distal end projecting from the cylindrical sleeve. The distal end has a push surface. The dual actuator has a longitudinal passage. A grip cage is provided having a cylindrical base and longitudinal fingers projecting distally from the cylindrical base forming a basket to retain the ball end. At least one pair of adjacent fingers defines a side opening for passing the ball end into the basket with a shaft extending from the ball located between distal ends of the fingers. A swage catch is longitudinally slidable in the central cavity and has distal end retained by the grip cage at an interior surface of the cylindrical base. The swage catch has a proximal end adapted to be drawn by a tension cable of the stabilizer arm. The dual actuator further includes a cantilevered spring arm with a detent at a distal end which flexes in a radial direction. The spring arm has an equilibrium position at which the longitudinal passage is open and a compressed position at which the detent partially closes the longitudinal passage. The grip cage includes an interior sloped surface for compressing the spring arm to the compressed position when the grip cage is pulled toward the cylindrical sleeve by the swage catch.

BRIEF DESCRIPTION OF THE DRAWINGS

FIG. 6 is an exploded view of the quick connect of FIG. 5.

FIG. 7 is a cross-sectional view of the exploded components of FIG. 6.

DETAILED DESCRIPTION OF PREFERRED EMBODIMENTS

Figure 1:
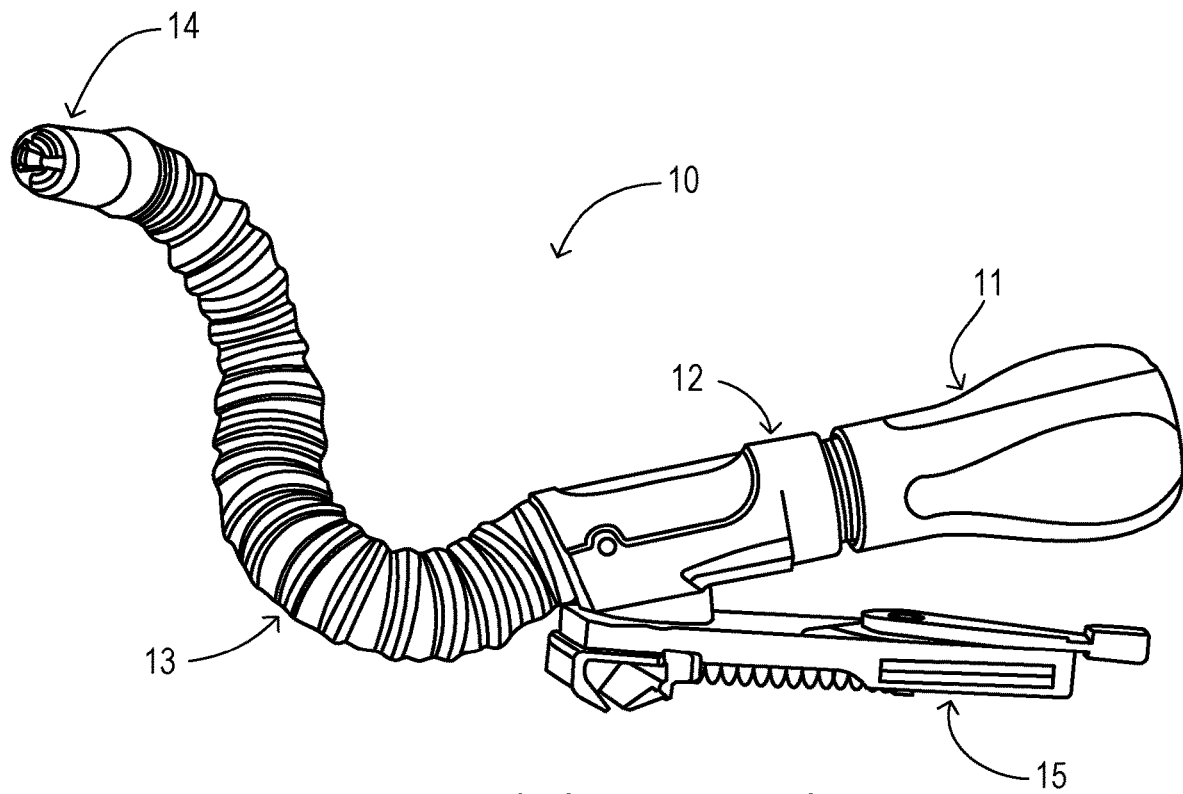
FIG. 1 is a side view of a prior art stabilizer arm with a ball-type quick connect.
Figure 2:
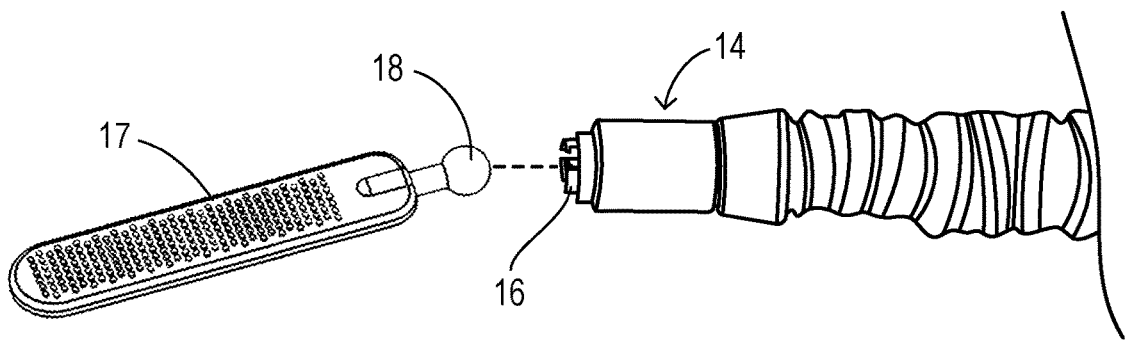
FIG. 2 is a side view of a retractor tool with a ball stem being mounted to the quick connect of FIG. 1.

FIGS. 1 and 2 show a known stabilizing arm 10 with a handle 11, base 12, articulating section 13, and quick-connect mount 14. A clamp assembly 15 attaches to a fixture of a sternal retractor, for example. A tension cable extends from a proximal end of the stabilizing arm (e.g., from the base or handle) to the distal end (e.g., the quick-connect mount or a final fixed link in the adjustable linkage). A solid, stranded cable or a fiber resin can be used. In the example of FIG. 1, an internal mechanism adjusts tension in the cable in response to rotation of handle 11. Articulating section 13 has a plurality of nested, semi-spherical links which can be rotated within one another to provide bends in the direction in which section 13 extends. When the cable is sufficiently slack, the links are slidable but when the cable is tightened then the links bind together and section 13 retains a desired trajectory.

As shown in FIG. 2, quick connect 14 is a ball-type mount with a collet 16 for receiving a ball stem 18 of a manipulator tool 17 (e.g., a malleable finger for grasping tissues). When the tension cable is slack, circumferentially-spaced fingers of collet 16 flex apart to accept insertion or removal of ball stem 18. After tightening of the tension cable, collet 16 retains tool 17 in a fixed configuration.

Figure 3:
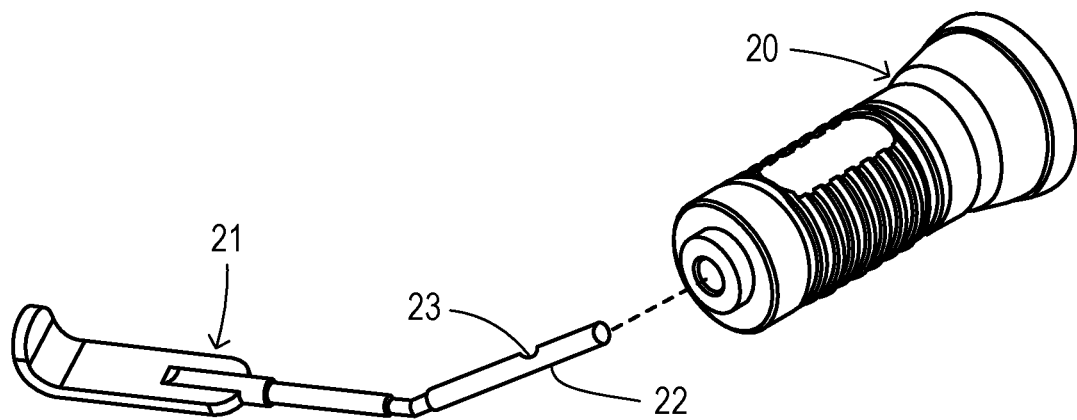
FIG. 3 is a side view of a retractor tool with an end shaft being mounted to a prior art shaft-type quick connect.
Figure 4:
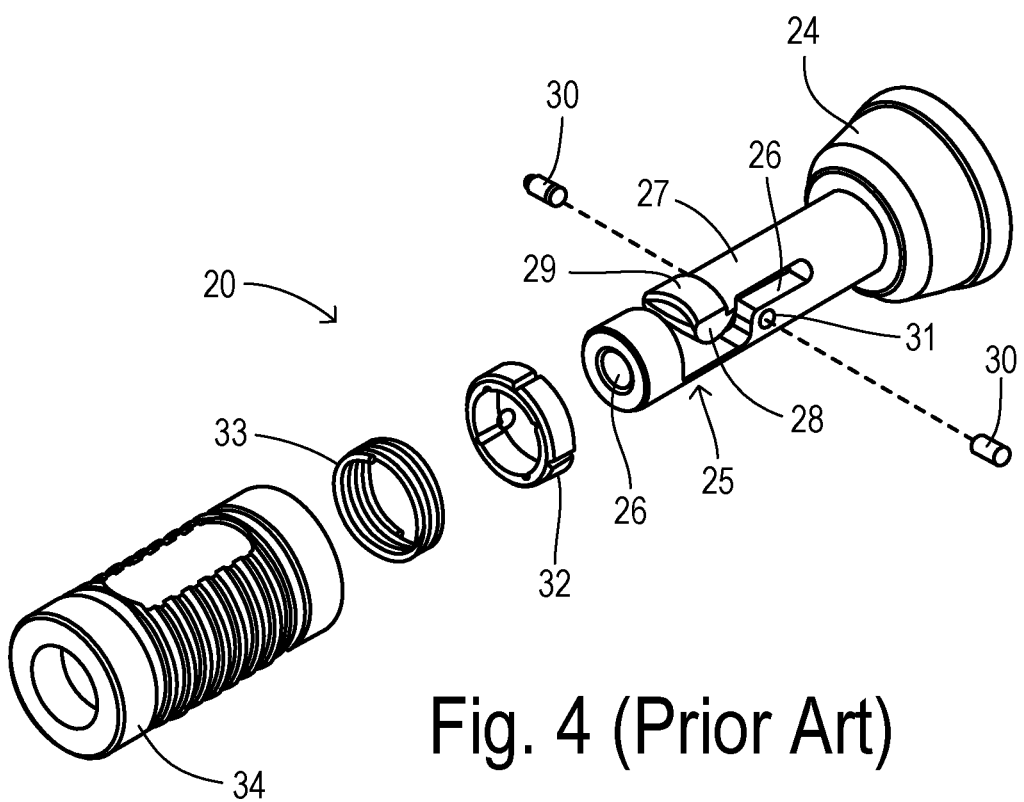
FIG. 4 is an exploded view of the shaft-type quick connect of FIG. 3.

FIGS. 3 and 4 show another commercially-available mounting system for manipulator tools on a stabilizer arm. As shown in FIG. 3, a shaft-type quick-connect mount 20 receives a manipulator tool 21 (e.g., malleable retractor finger) having a mounting shaft 22 at its distal end. Shaft 22 may preferably include a notch 23 along part of its circumference to be captured by a latch or pin within a socket of quick-connect 20.

FIG. 4 provides an exploded view of mount 20, wherein a base 24 (which is itself attached to an end link of the articulating section of the stabilizer arm) supports a casing 25 defining a hollow passage 26 acting as a socket to receive shaft 22. Passage 26 extends to an outer radial surface at medial portion of casing 25 to form a flexible spring arm or beam 27. At the end of spring arm 27, a detent 28 projects radially inward and a cam surface 29 projects radially outward. In its undeflected (relaxed) state, spring arm 27 is in a position wherein detent 28 does not intrude into passage 26 (i.e., longitudinal insertion/removal of a tool shaft within passage 26 is unobstructed). An inward radial force on cam surface 29 deflects detent 28 into passage 26 for retaining shaft 22 of tool 21. Preferably, notch 23 receives detent 28 for positive locking of shaft 22, but locking can alternatively be achieved by compression of detent 28 against a cylindrical shaft without a notch.

For selectably compressing cam surface 29, a tubular collar 34 is provided. Two pegs 30 are installed in holes 31 to project radially from casing 25 and are received in axial guide slots in an inner hollow surface of collar 34 to guide the axial sliding of collar 34 over casing 25. An inner diameter of tubular collar 34 is tapered so that it is larger at a proximal end and gradually reduces toward the proximal end of collar 34 (opposite base 24). A spring 33 is attached between collar 34 and casing 25 (or base 24) such that spring 33 pulls collar 34 over casing 25 against or toward base 24. An aluminum ring 32 may be affixed at base 24 to hold the assembly together. Interference between cam surface 29 and the tapered portion of collar 34 presses down on spring arm 27 causing detent 28 to project into passage 26. This prevents an attached tool from being inserted or removed until collar 34 is manually pulled away from base 24. Once collar 34 is pulled up, the internal taper collar 34 no longer applies pressure to spring arm 27, and tool shaft 22 can be inserted or removed very easily. When the user stops pulling on collar 34, spring 33 pulls it back down over cam surface 29, thereby locking detent 28 in place.

In order to operate with quick-connect mount 20, a manipulator tool is made with an end shaft (with or without a notch). Since a ball cannot be included at the end of the shaft, such a tool is incompatible with a ball-type quick-connect mount with a collet as shown in FIGS. 1 and 2. The invention provides a hybrid quick connect mechanism that can grasp the end shaft of a manipulator tool with either a shaft end or a ball end.

The present invention provides a quick connect mechanism permanently installed at the distal end of a stabilizer arm. The quick connect mechanism is compatible with both ball-style and shaft-style attachments, and it interfaces with the spherically shaped links while anchoring the distal end of the tension cable.

Figure 5:
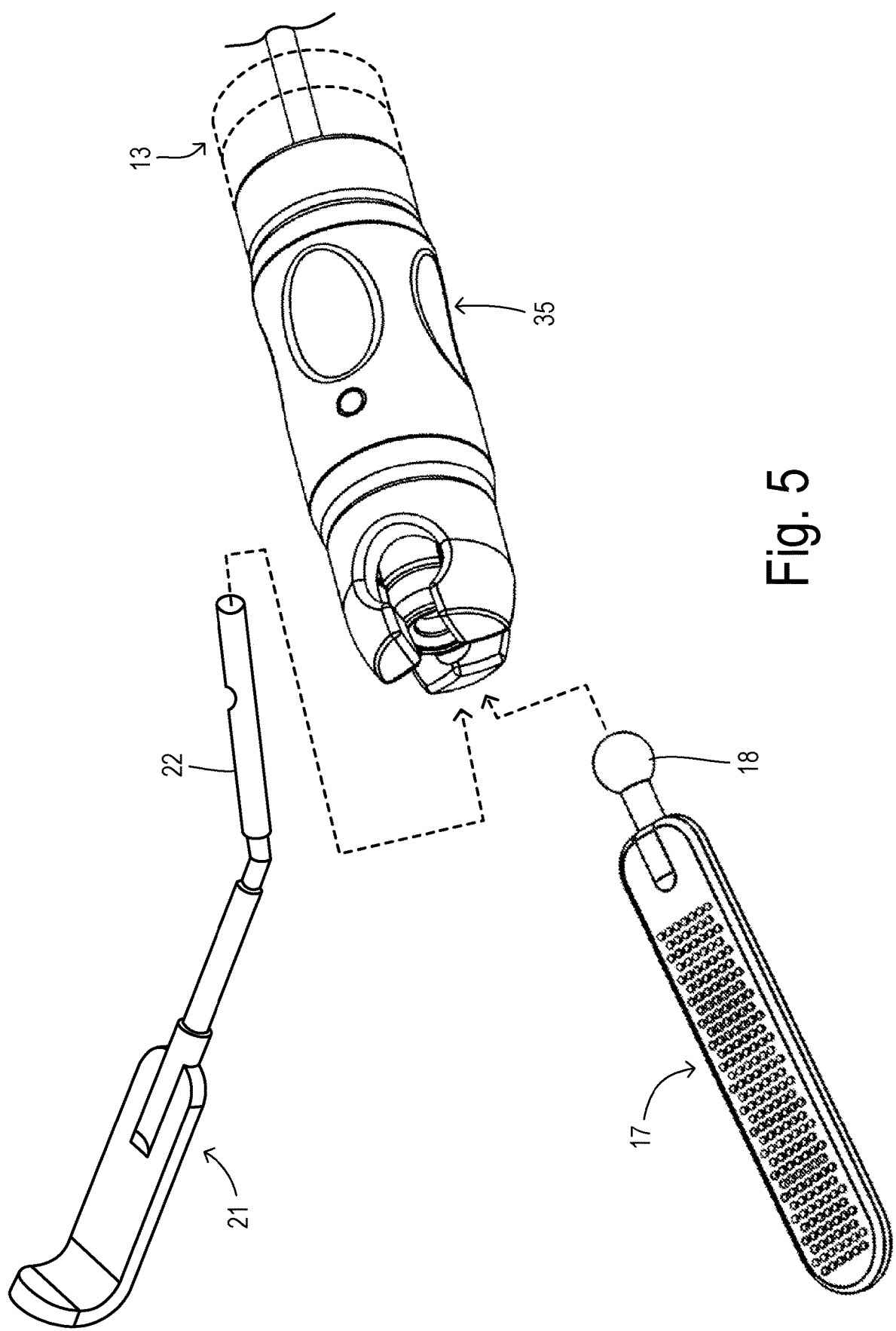
FIG. 5 is a perspective view of a hybrid quick connect mechanism capable of accepting either a ball-type or shaft-type manipulation tool.
Figure 8:
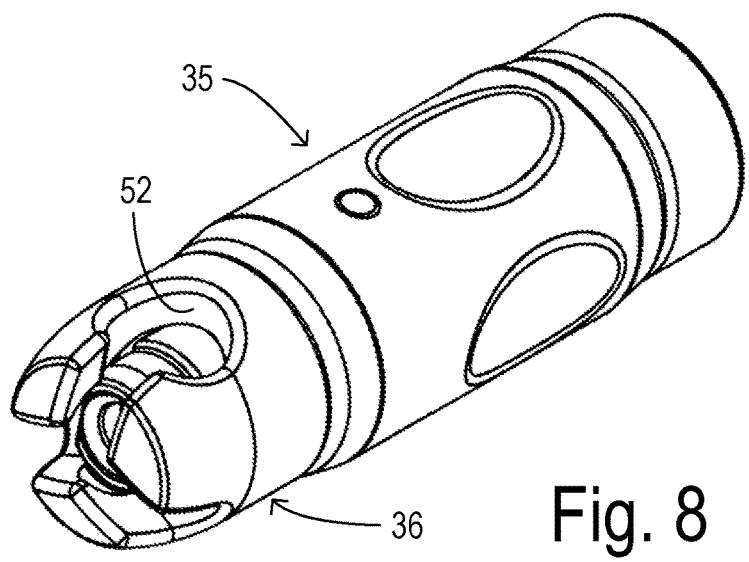
FIG. 8 is a perspective view of the quick connect of FIG. 5 in a closed state.

FIGS. 5-24 show a first embodiment of a quick connect 35 placed at a distal end of a series of articulating links 36. As shown in FIG. 5, quick connect 35 accepts either the ball stem 18 of manipulator tool 17 or the shaft 22 of manipulator tool 21.

The exploded views of FIGS. 6 and 7 show the components of quick connect 35, including a grip cage 36, a cylindrical sleeve 37, a dual actuator 38, a swage catch 39, a compression spring 40, a swage 41, and a first link body 42. Each of the components may preferably be comprised of metal (e.g., machined stainless steel). Swage catch 39 may be formed of hardened steel. In some embodiments, some components may be alternatively be made of molded thermoplastic.

Swage 41 is affixed at the distal end of a tension cable 43. A pair of pins 44 affix dual actuator 38 to cylindrical sleeve 37 such that a proximal end 47 is fixed in central cavity 45 and a distal end 46 projects from cylindrical sleeve 37 into grip cage 36. As seen in FIG. 7, a pin 44 may be press fit in an aperture 50 through sleeve 37 and extends into a recess 51 to lock dual actuator 38 in place. Dual actuator 38 has a push surface 48 at distal end 46 (for retaining a ball-end manipulator tool) and has a longitudinal passage 49 (for receiving a shaft-end manipulator tool). Push surface 48 preferably has a concave spherically-shaped surface profile matching the ball end.

Figure 9:
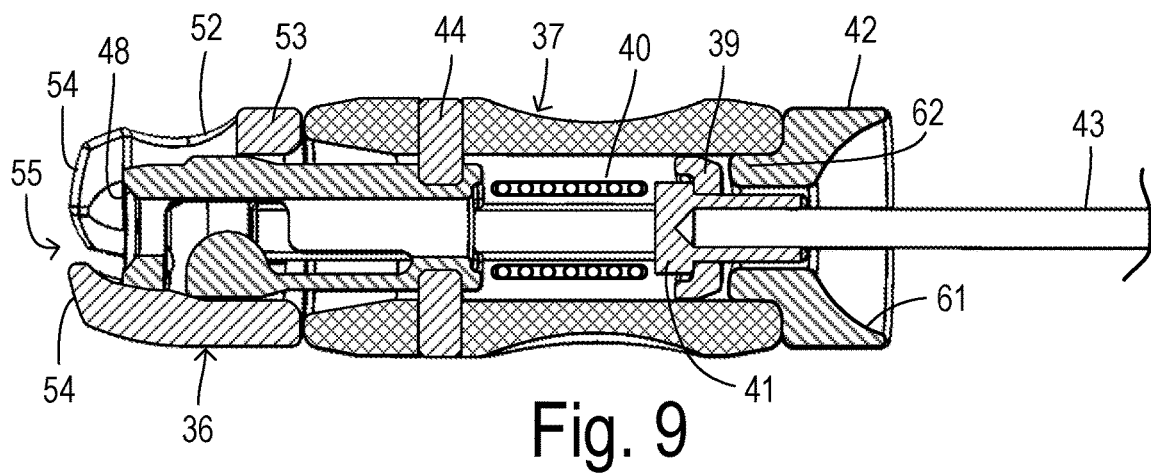
FIG. 9 is a cross-sectional view of the quick connect in the closed state.
Figure 10:
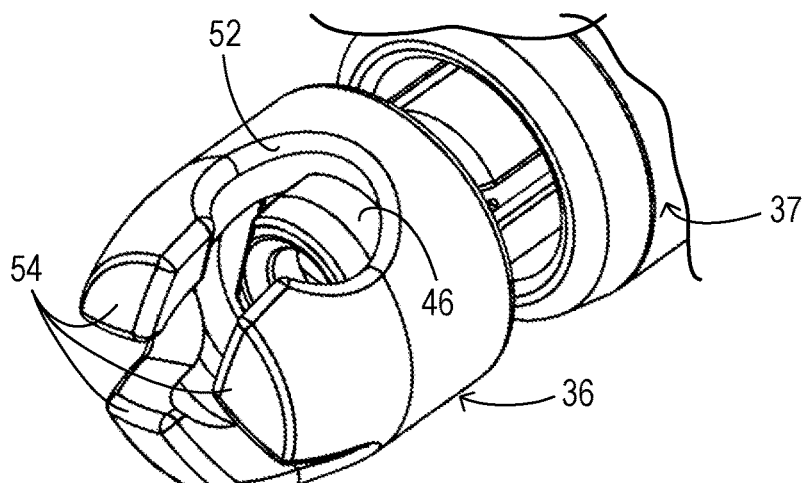
FIG. 10 is a perspective view of the distal end of the quick connect in an opened state.

The manner of retaining a ball-end tool will be described in connection with FIGS. 8-14. For inserting the ball-end tool, quick connect 35 may be held in the orientation shown in FIG. 8 so that a side opening 52 is on a top side. As shown in FIG. 9, grip cage 36 has a cylindrical base 53 and longitudinal fingers 54 projecting distally from cylindrical base 53 to form a basket 55 to retain the ball end. Side opening 52 is spaced away from the distal tip of grip cage 36 and between one pair of adjacent fingers 54. Grip cage 36 is extendable from sleeve 37 and from distal end 46 of dual actuator 38 (FIG. 10) to unblock side opening 52, allowing the ball-end of the tool into the basket. An opening between fingers 54 along a central axis of quick connect 35 receives a shaft that extends from the ball.

Figure 13:
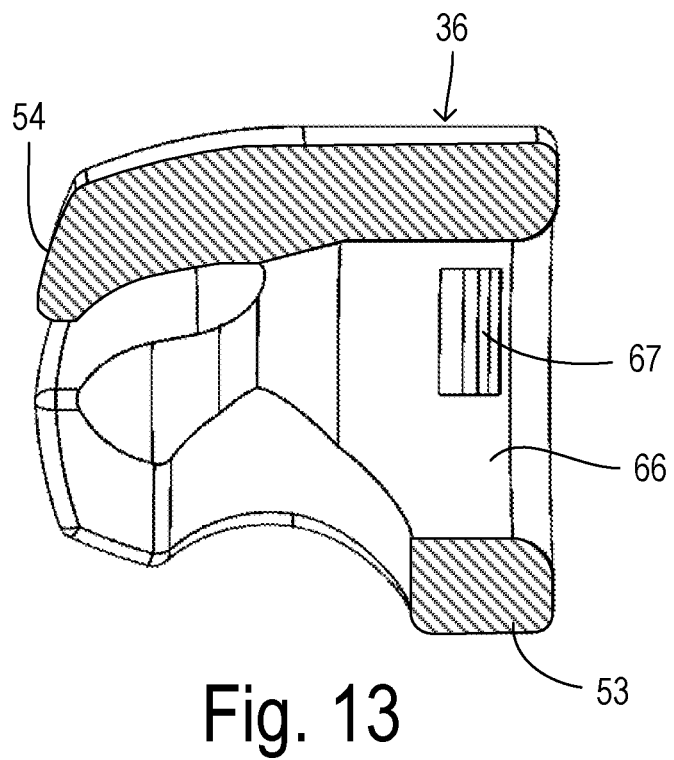
FIG. 13 is a vertical cross section of the grip cage.
Figure 14:
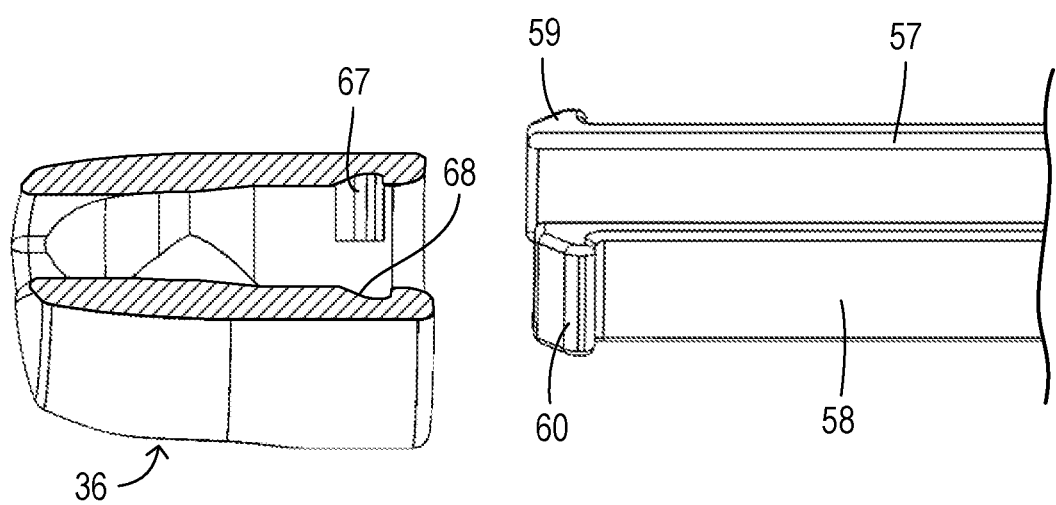
FIG. 14 is a horizontal cross section of the grip cage and a swage catch prior to installation onto the grip cage.
Figure 15:
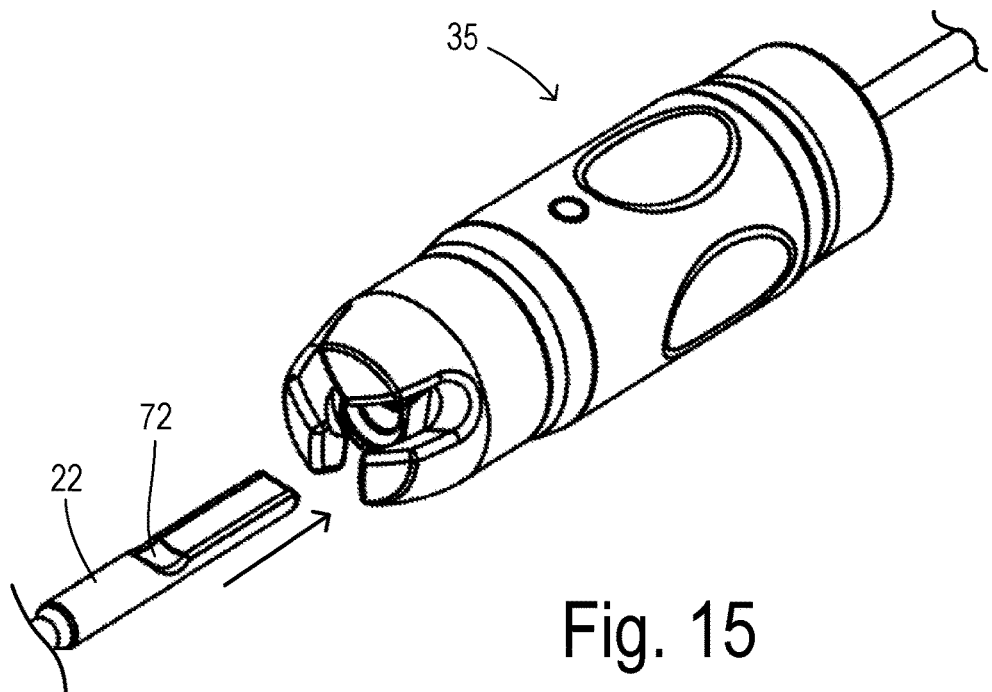
FIG. 15 is a perspective view of the quick connect of FIG. 8 re-oriented to receive a shaft-type manipulator tool.
Figure 16:
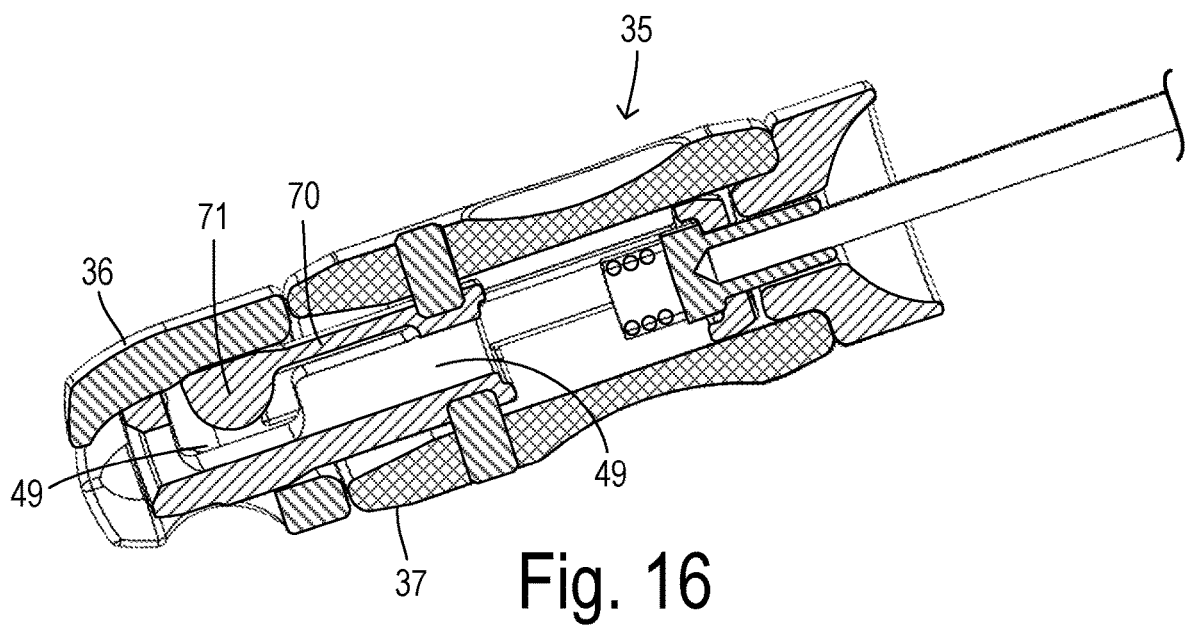
FIG. 16 is a vertical cross section of the re-oriented quick connect of FIG. 15

In a fully retracted state shown in FIG. 9, base 53 of grip cage 36 abuts a distal end of sleeve 37. Swage catch 39 is longitudinally slidable in central cavity 45 and has a distal end retained by grip cage 36 at an interior surface of cylindrical base 53. A proximal end of swage catch 39 is configured to be drawn in a proximal direction by tension cable 43 which is captured by swage 41 at an interior portion of swage catch 39. Swage catch 39 is comprised of an annulus or ring 56 at the proximal end, a pair of longitudinal arms 57 and 58 extending distally from annulus 56, and a pair of barbs 59 and 60 extending radially outward at the distal ends of arms 57 and 58 to be captured by grip cage 36. As shown in FIGS. 13 and 14, cylindrical base 53 has an interior surface 66 into which a pair of notches 67 and 68 are formed which capture barbs 59 and 60 of swage catch 39 so that grip cage 36 and swage catch 39 always move in tandem.

First link body 42 has a spherical proximal face 61 adapted to interface with the series of articulating links. A distal hub 62 of body 42 aligns and retains cylindrical sleeve 37 in the retracted state when tension cable 43 is under tension. In addition, swage catch 39 is drawn proximally until grip cage 36 is prevented from further movement (e.g., by contacting sleeve 37).

Figure 11:
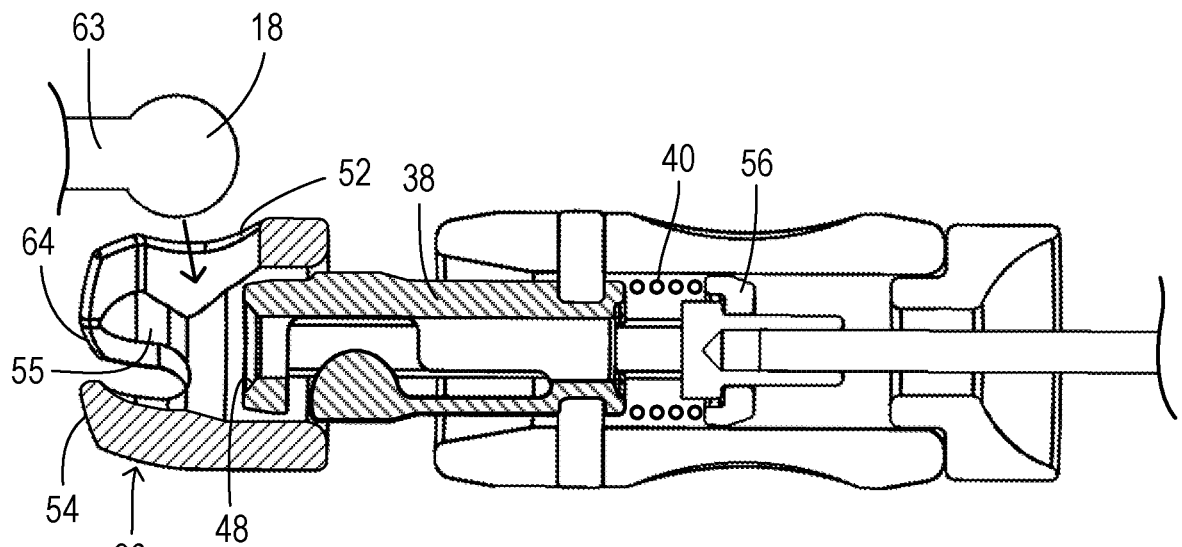
FIG. 11 is a longitudinal cross section of the quick connect in an open state for inserting a ball-type manipulator tool.

When tension cable 43 is loosened, grip cage 36 can be extended as shown in FIG. 11 (e.g., by manually pulling grip cage 36 distally). The forward movement also pulls annulus 56 distally and compresses spring 40 between annulus 56 and dual actuator 38. Ball 18 can be lowered into interior basket 55 in grip cage 36 via side opening 52. A shaft 63 projecting from ball 18 is retained between the distal tips of fingers 54. Fingers may have a pointed profile for guiding shaft 63 into alignment with a central axis of quick connect 35 at a center opening 64.

Figure 12:
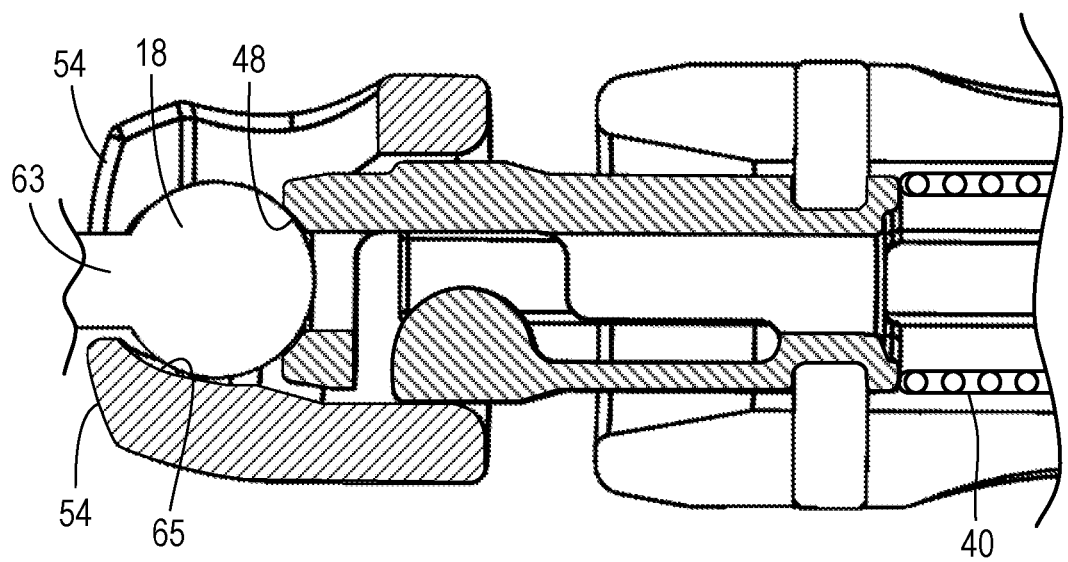
FIG. 12 is a cross-sectional view of the quick connect with the ball-type tool fully captured and locked.

With ball 18 inserted, grip cage 36 can be released so that compression spring 40 expands, thereby urging grip cage 36 to move proximally as shown in FIG. 12. Spring 40 provides enough force to gently hold ball 18 is position without moving under its own weight but allowing adjustments of its position, e.g., by rotating around the axis of shaft 63 (while tension cable 43 may be slightly tight during adjustment of the articulating links). When cable 43 is brought under greater tension, then grip cage 36 is retracted with greater force. Fingers 54 have an interior sloped surface 65 enclosing a portion of basket 55 so that retraction of grip cage 36 compresses ball 18 between sloped surface 65 and push surface 48 of dual actuator 38, locking it in place.

To summarize the ball-end attachment, a handle of the stabilizer arm can be adjusted to loosen tension cable 43. A user pulls back cylindrical sleeve 37 from grip cage 36, which compresses spring 40 and allows the ball to be placed through round side opening 52. When sleeve 37 is released, spring 40 pushes dual actuator 38 forward, which will press the ball forward to the front of grip cage 36. When tension cable 43 is tightened, first link body 42 will push sleeve 37 and actuator 38 forward, locking the ball against fingers 54 of grip cage 36.

The manner of retaining a shaft-end tool will be described in connection with FIGS. 15-18. For inserting the shaft-end tool, quick connect 35 may be held in the orientation shown in FIG. 15 with the side opening for inserting a ball end facing downward (i.e., rotated by 180° from the orientation shown in FIG. 8). One reason for this orientation is to position a cantilevered spring arm 70 (FIG. 16) toward the top of quick connect 35 whenever a shaft 22 of the shaft-end tool includes retention features for being specifically engaged by spring arm 70 (e.g., a notch 72). In particular, spring arm 70 carries a detent 71 at a distal end which flexes in a radial direction. Spring arm 70 has an equilibrium position at which longitudinal passage 49 is open (FIG. 17) and a compressed position (FIG. 18) at which detent 71 partially closes longitudinal passage 49. Sloped surface 65 inside grid cage 36 controls the radial position of detent 71 as grip cage extends and retracts. For example, interior sloped surface 65 compresses spring arm 70 radially inward when grip cage 36 abuts sleeve 37 in the fully retracted state shown in FIG. 16.

Figure 17:
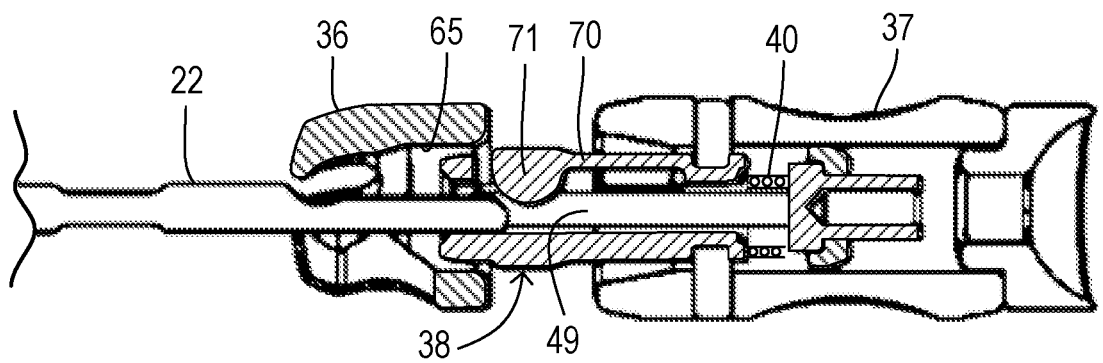
FIG. 17 is a cross-sectional view of the quick connect of FIG. 15 is an opened state for receiving the tool.
Figure 18:
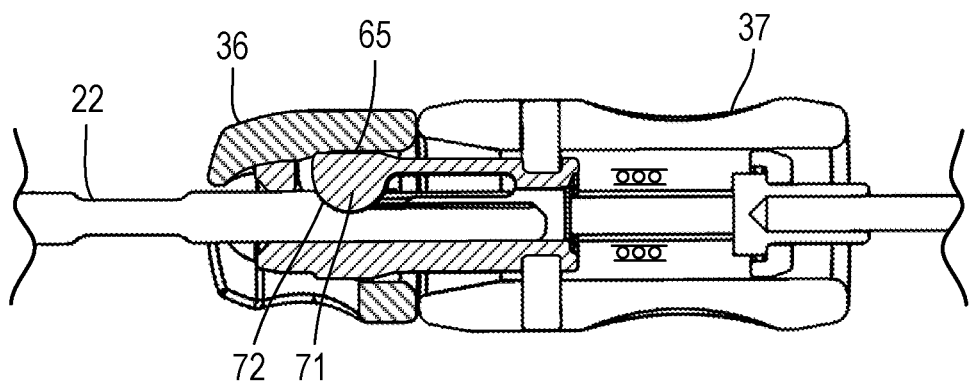
FIG. 18 is a cross-sectional view of the quick connect of FIG. 17 after full insertion and locking of the shaft-type tool.

To connect shaft 22 of the tissue manipulator tool, the tension cable is adjusted to a loose condition. Cylindrical sleeve 37 and grip cage 36 are pulled apart, compressing spring 40 and allowing radial clearance for spring arm 70 to deflect outward while shaft 22 is inserted. The equilibrium position of spring arm 70 and detent 71 may be arranged to clear longitudinal passage 49, or if passage 49 is still partially blocked then the advance of shaft 22 can deflect detent 71 outward by the amount necessary. Attachment shaft 22 is inserted through grip cage 36 and into passage 49 within dual actuator 38 (FIG. 17). A proximal end of shaft 22 lifts spring arm detent 71 and continues proximally until detent 71 eventually settles into indent 72 of shaft 22. As shown in FIG. 18, the releasing of sleeve 37 and grip cage 36 allows compression spring 40 to expand and help push dual actuator 38 forward (with respect to grip cage 36). When the stabilizer arm handle is turned to tighten the tension cable, first link body 42 pushes sleeve 37 and dual actuator 38 forward, locking the manipulator tool by preventing spring arm 70 from opening due to sloped surface 65 of grip cage 36.

Figure 19:
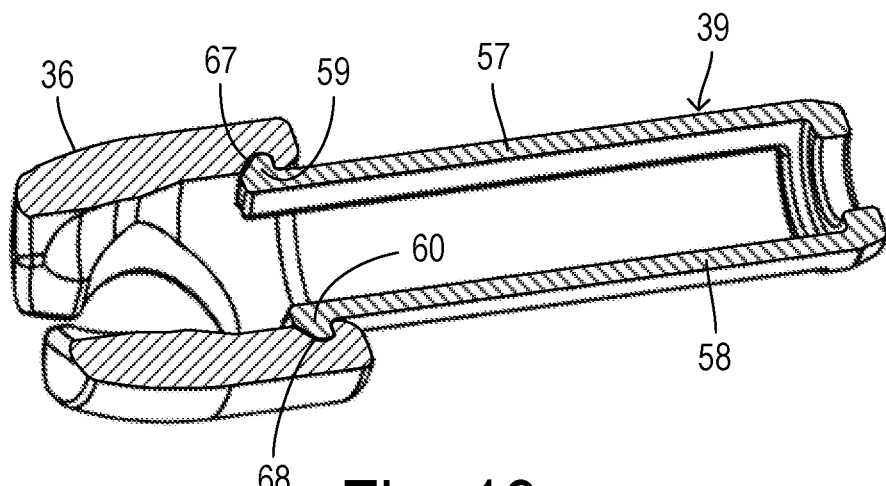
FIGS. 19-24 are cross-sectional views of the quick connect mechanism in an assembly sequence.
Figure 20:
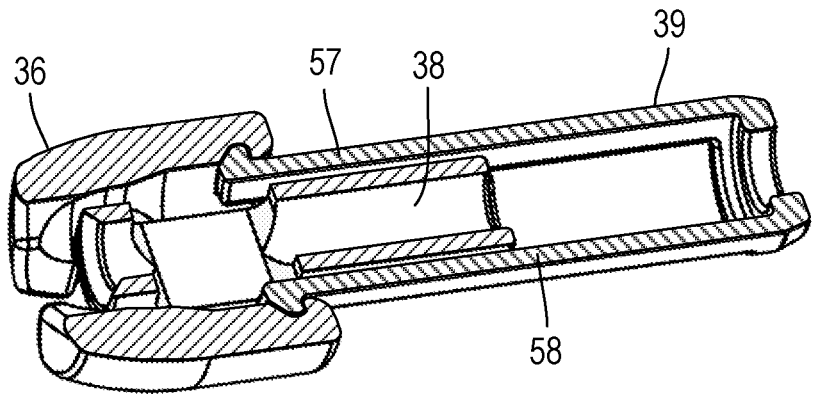
Figure 21:
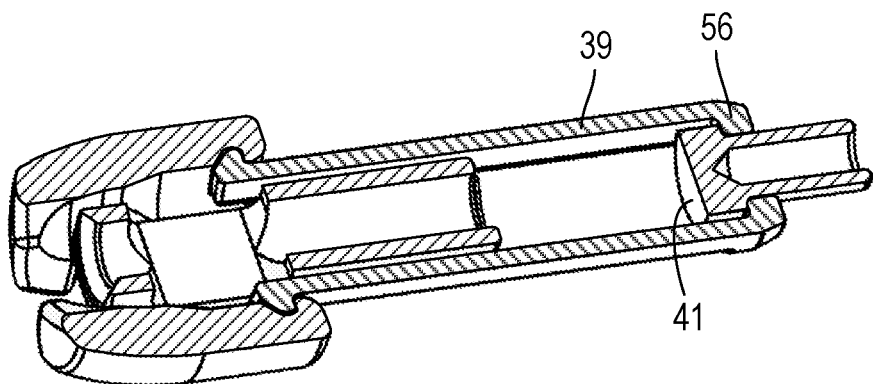
Figure 22:
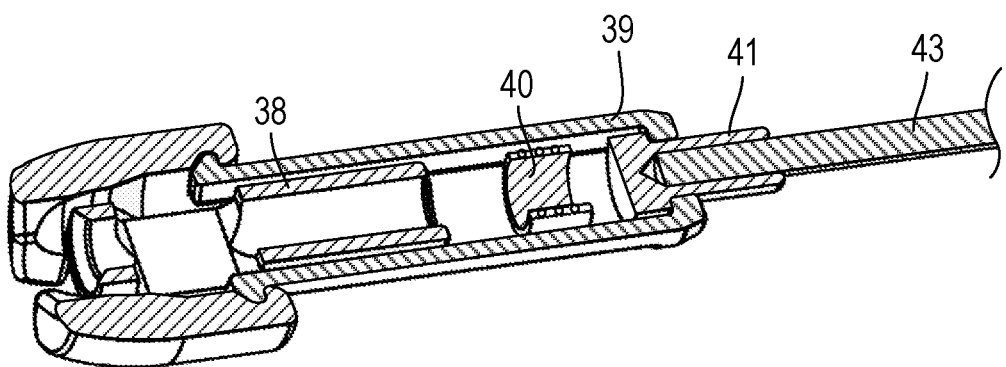
Figure 23:
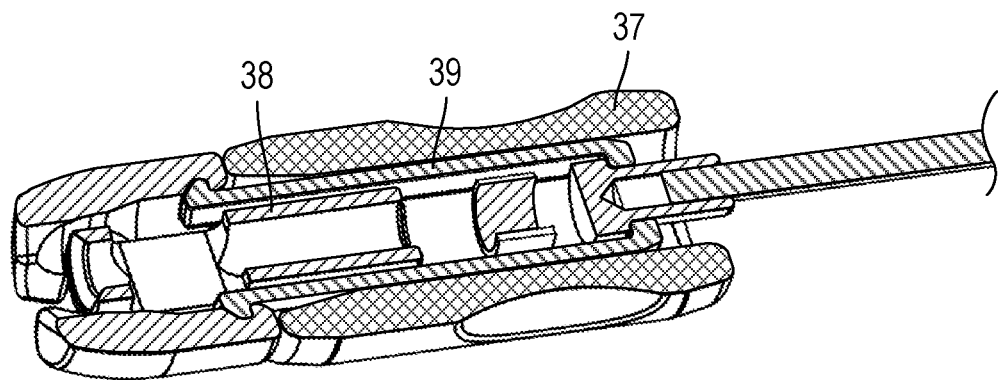
Figure 24:
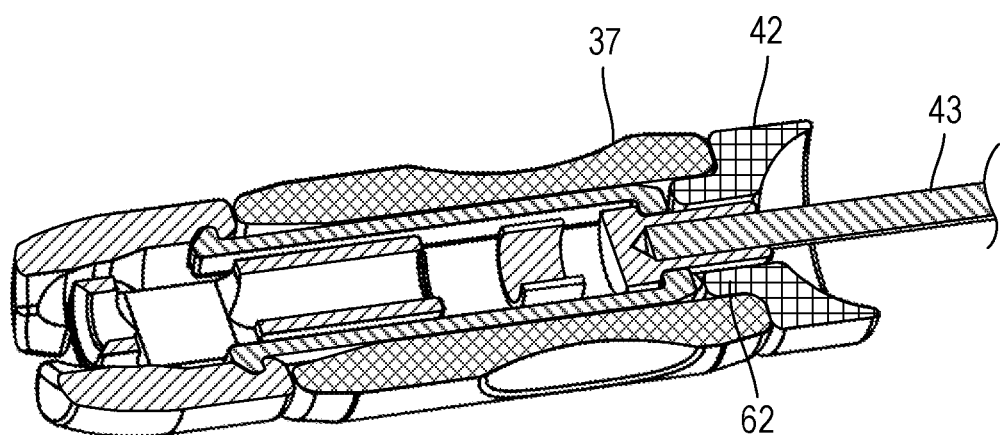
Figure 25:
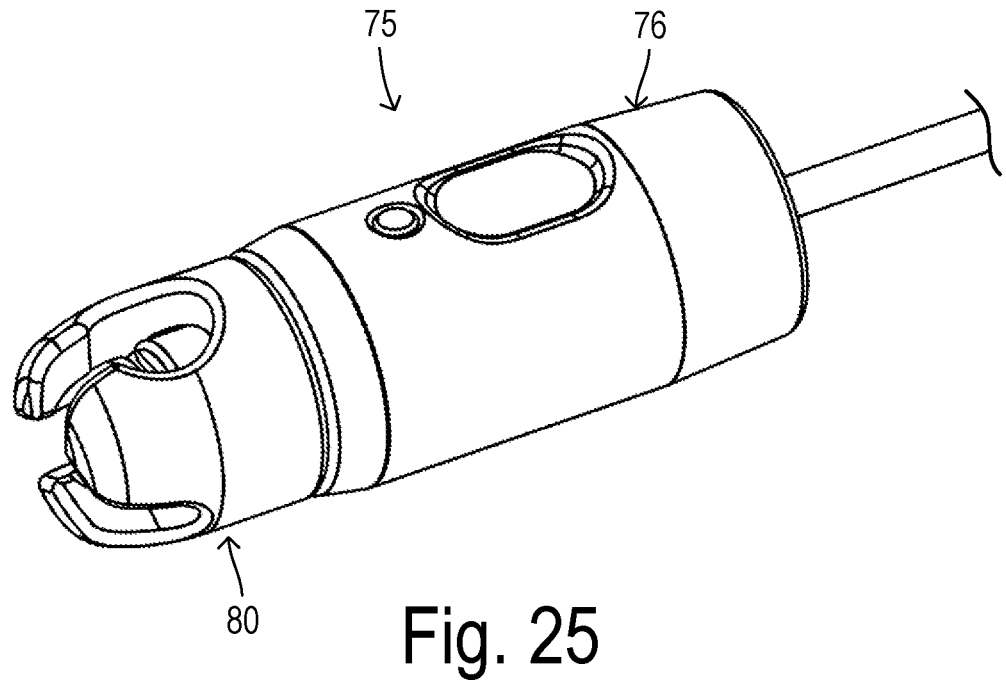
FIG. 25 is a perspective view of another embodiment of a quick connect mechanism.

FIGS. 19-24 provide an example method for assembling quick connect mechanism 35. In FIG. 19, barbs 59 and 60 of swage catch 39 are inserted into to grooved notches 67 and 68 inside grip cage 36. Arms 57 and 58 may flex radially inward to facilitate insertion into grip cage 36. In FIG. 20, dual actuator 38 is dropped through swage catch 39 (between arms 57 and 58) into grip cage 36 (it is ensured that a top side of actuator 38 is opposite the side opening of grip cage 36 which is used for inserting a ball-end of a manipulator tool). In FIG. 21, swage 41 is inserted through a center hole of annulus 56 of swage catch 39. In FIG. 22, tension cable 43 is affixed to swage 41 (e.g., by crimping) and compression spring 40 is inserted between swage 41 and dual actuator 38. In FIG. 23, cylindrical sleeve 37 is placed over swage catch 39. The two apertures (e.g., aperture 50 in FIG. 7) of sleeve 37 are lined up with matching recesses or holes in actuator 38 (e.g., recess 51 in FIG. 7) so that pins (e.g., pins 44 in FIG. 7) can be inserted through sleeve 37 and welded or press fit (not shown) in order to rigidly hold sleeve 37 to actuator 38. In FIG. 24, tension cable is fed through first link body 42, and hub 62 is inserted into sleeve 37. The remainder of the articulating links (e.g., alternating ball links and cup links) are assembled onto cable 43 and a handle with associated components are added.

Figure 26:
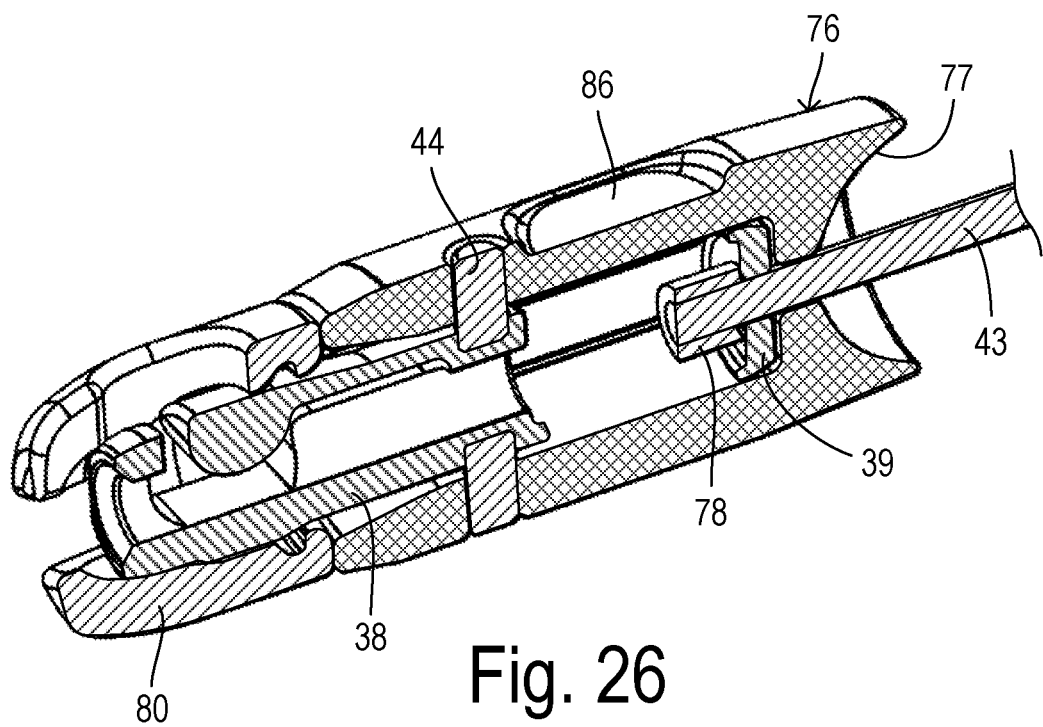
FIG. 26 is a vertical cross section of the quick connect of FIG. 25.
Figure 27:
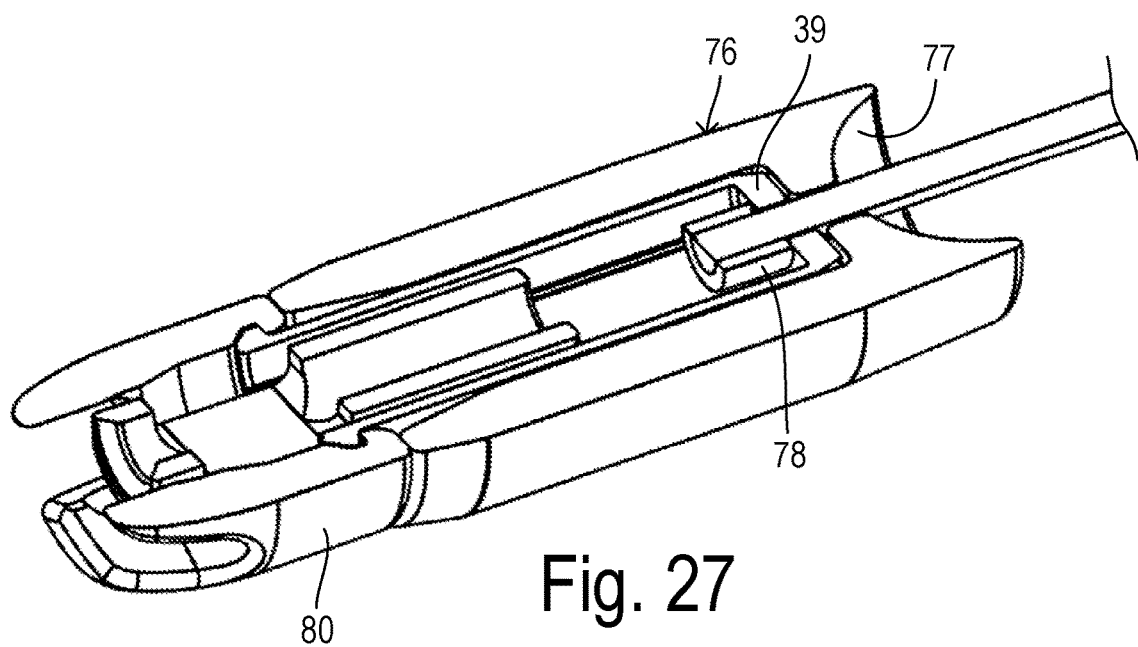
FIG. 27 is a horizontal cross section of the quick connect of FIG. 25.

FIG. 25-29 show a second embodiment of a quick connect mechanism 75 (sharing many identical characteristics with the first embodiment). Only the differences are described below. In particular, a cylindrical sleeve 76 integrates the function of a first link body by virtue of a spherical socket-end 77 configured to receive a typical ball-end link of the articulating links as shown in FIGS. 26 and 27. Instead of a swage the extend partially through an annulus of swage catch 39, a swage ring 78 is crimped to tension cable 43 inside swage catch 39. As a result, a compression spring (not shown) may bear directly against an interior surface of the annulus and against dual actuator 38.

Figure 28:
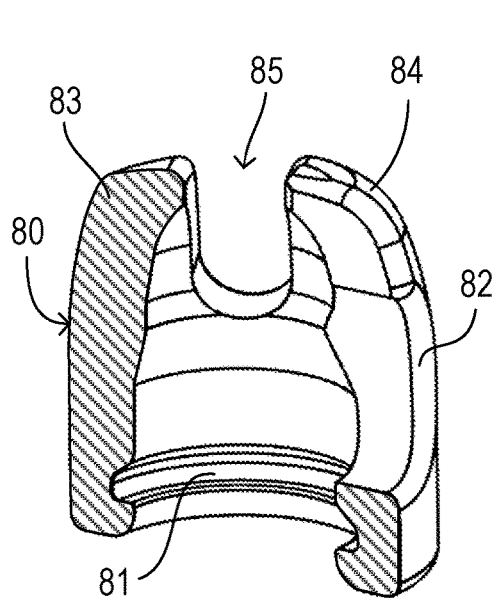
FIG. 28 is a cross-sectional view of the grip cage of FIG. 25.
Figure 29:
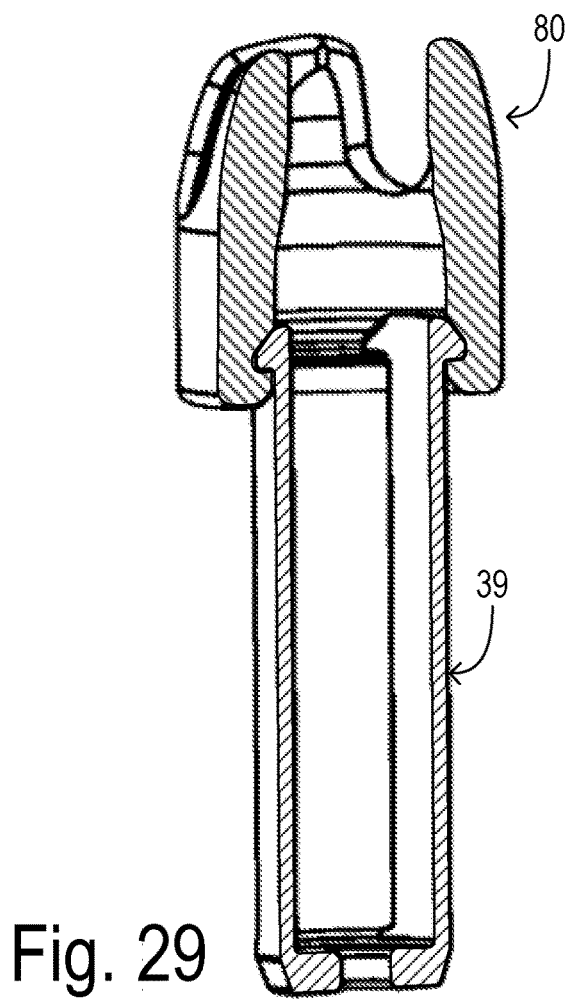
FIG. 29 is a cross-sectional view of the grip cage and swage catch of FIG. 25.

In one aspect of the second embodiment, a grip cage 80 can rotate freely, no longer requiring entire device to be rotated 180° to switch from a ball connection to a shaft connection. As shown in FIGS. 28 and 29, grip cage 80 has a cylindrical base which includes an annular groove 81. Curved fingers 83 and 84 have an intervening slot 85. A side opening 82 is adapted to receive a ball-end attachment. A shape of groove 81 is adapted to capture the barbs of swage catch 39 and to permit rotation of grip cage 80 on swage catch 39. Thus, an orientation of grip cage 80 can be manually rotated to place opening 82 at any convenient position to insert a manipulator tool.

For the purpose of finding the correct orientation for inserting a shaft-end tool, cylindrical sleeve 76 carries a visual indicator indicating an orientation of the detent of the dual actuator to facilitate insertion of a manipulator tool such that a notch in the shaft end is in alignment with the detent. For example, a depression 86 in an outer surface of sleeve 76 (FIG. 26) is formed alongside a pin 44 which holds a top side of actuator 38 (i.e., since the position of grip cage 80 no longer provides an indication of the orientation of actuator 38).

Figure 30:
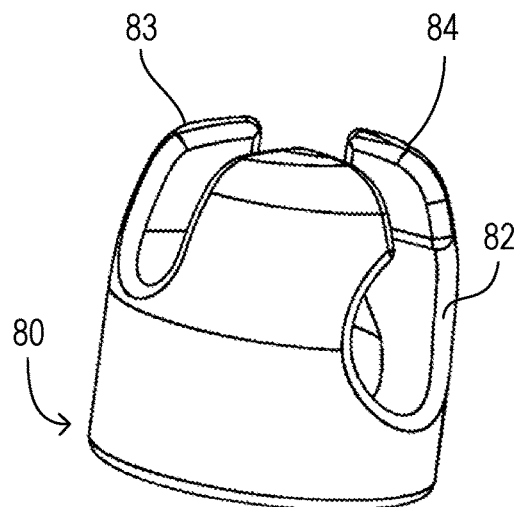
FIG. 30 is a side view of the grip cage.
Figure 31:
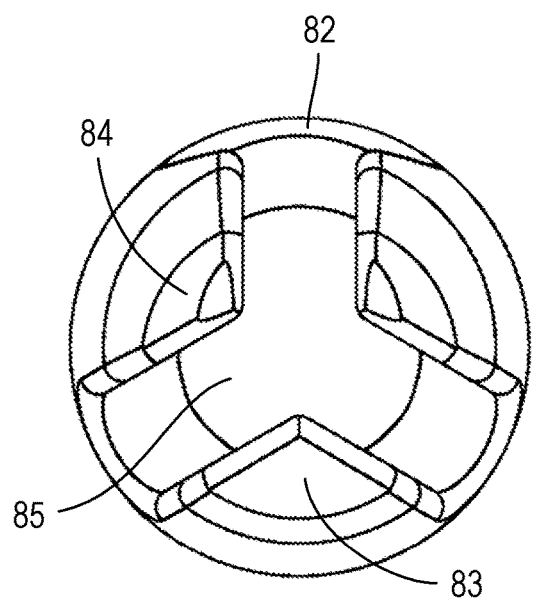
FIG. 31 is an end view of the grip cage.
Figure 32:
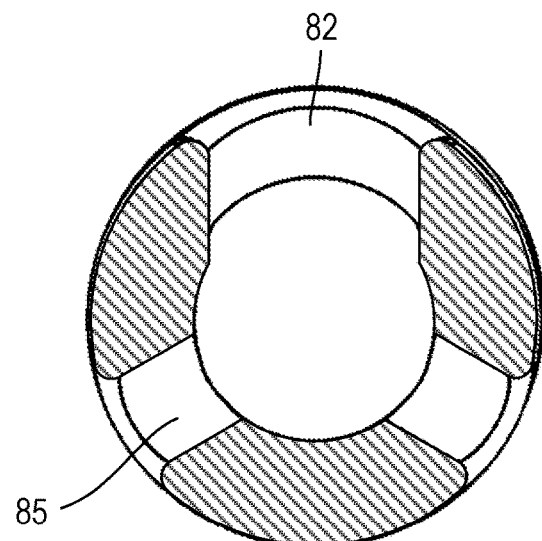
FIG. 32 is an end cross section of the grip cage.

As shown in FIGS. 30-32, a single side opening 82 has been shown for insertion of a ball-end tool. However, any or all of the openings between adjacent fingers (such as opening 85) could be enlarged in order to provide multiple side openings adapted to receive the ball-end attachments.

What is claimed is:

1. A surgical stabilizer arm configurable to retain tissue manipulator tools with either a shaft end or a ball end, comprising:
   a cylindrical sleeve with a central cavity;
   a dual actuator having a proximal end fixed in the central cavity and a distal end projecting from the cylindrical sleeve, wherein the distal end has a push surface, and wherein the dual actuator has a longitudinal passage;
   a grip cage having a cylindrical base and longitudinal fingers projecting distally from the cylindrical base forming a basket to retain the ball end, wherein at least one pair of adjacent fingers defines a side opening for passing the ball end into the basket with a shaft extending from the ball located between distal ends of the fingers; and
   a swage catch longitudinally slidable in the central cavity having a distal end retained by the grip cage at an interior surface of the cylindrical base, and having a proximal end adapted to be drawn by a tension cable of the stabilizer arm;
   wherein the dual actuator further includes a cantilevered spring arm with a detent at a distal end which flexes in a radial direction, wherein the spring arm has an equilibrium position at which the longitudinal passage is open and a compressed position at which the detent partially closes the longitudinal passage; and
   wherein the grip cage includes an interior sloped surface for compressing the spring arm to the compressed position when the grip cage is pulled toward the cylindrical sleeve by the swage catch.

2. The stabilizer arm of claim 1 wherein the proximal end of the swage catch has an aperture for receiving the tension cable, further comprising:
   a swage adapted to be captured on the tension cable inside the swage catch and allowing the tension cable to slide distally through the aperture of the swage catch when the tension cable is not under tension.

3. The stabilizer arm of claim 1 wherein the swage catch comprises:
   a proximal annulus;
   a pair of longitudinal arms extending from the annulus; and
   a pair of barbs extending radially outward at the distal ends of the arms to engage the grip cage.

4. The stabilizer arm of claim 3 wherein the cylindrical base of the grip cage includes a pair of notches in the interior surface capturing the barbs.

5. The stabilizer arm of claim 3 wherein the cylindrical base of the grip cage includes an annular groove capturing the barbs and permitting rotation of the grip cage on the swage catch.

6. The stabilizer arm of claim 1 further comprising:
   a compression spring disposed between the dual actuator and the swage catch to urge the dual actuator toward the grip cage.

7. The stabilizer arm of claim 6 further comprising:
   a swage adapted to be captured on the tension cable inside the swage catch and allowing the tension cable to slide distally through an aperture in the swage catch when the tension cable is not under tension;
   wherein the compression spring bears against the swage and the dual actuator.

8. The stabilizer arm of claim 1 wherein the push surface of the dual actuator has a concave spherical shape to capture the ball end.

9. The stabilizer arm of claim 1 further comprising a first link body having a spherical proximal face adapted to interface with a series of articulating links and having a distal hub aligning and retaining the cylindrical sleeve when the tension cable is under tension.

10. The stabilizer arm of claim 1 wherein the dual actuator is fixed to the cylindrical sleeve by radial pins.

11. The stabilizer arm of claim 1 wherein the cylindrical sleeve carries a visual indicator indicating an orientation of the detent of the dual actuator to facilitate insertion of a manipulator tool such that a notch in the shaft end is in alignment with the detent.

12. A surgical stabilizer system, comprising:
a handle;
a quick connect mechanism for holding tissue manipulator tools with either a shaft end or a ball end;
a plurality of successive articulating links each having a center opening; and
a tension cable extending through the center openings between the handle and the quick connect adapter;
wherein the quick connect mechanism is comprised of:
a cylindrical sleeve with a central cavity;
a dual actuator having a proximal end fixed in the central cavity and a distal end projecting from the cylindrical sleeve, wherein the distal end has a push surface, and wherein the dual actuator has a longitudinal passage;
a grip cage having a cylindrical base and longitudinal fingers projecting distally from the cylindrical base forming a basket to retain the ball end, wherein at least one pair of adjacent fingers defines a side opening for passing the ball end into the basket with a shaft extending from the ball located between distal ends of the fingers; and
a swage catch longitudinally slidable in the central cavity having a distal end retained by the grip cage at an interior surface of the cylindrical base, and having a proximal end adapted to be drawn by the tension cable toward the handle;
wherein the dual actuator further includes a cantilevered spring arm with a detent at a distal end which flexes in a radial direction, wherein the spring arm has an equilibrium position at which the longitudinal passage is open and a compressed position at which the detent partially closes the longitudinal passage; and
wherein the grip cage includes an interior sloped surface for compressing the spring arm to the compressed position when the grip cage is pulled toward the cylindrical sleeve by the swage catch.

13. The stabilizer system of claim 12 wherein the proximal end of the swage catch has an aperture for receiving the tension cable, the stabilizer system further comprising:
a swage captured on the tension cable inside the swage catch and allowing the tension cable to slide distally through the aperture of the swage catch when the tension cable is not under tension.

14. The stabilizer system of claim 12 wherein the swage catch comprises:
a proximal annulus;
a pair of longitudinal arms extending from the annulus; and
a pair of barbs extending radially outward at the distal ends of the arms to engage the grip cage.

15. The stabilizer system of claim 14 wherein the cylindrical base of the grip cage includes a pair of notches in the interior surface capturing the barbs.

16. The stabilizer system of claim 14 wherein the cylindrical base of the grip cage includes an annular groove capturing the barbs and permitting rotation of the grip cage on the swage catch.

17. The stabilizer system of claim 12 further comprising:
a compression spring disposed between the dual actuator and the swage catch to urge the dual actuator toward the grip cage.

18. The stabilizer system of claim 12 wherein the push surface of the dual actuator has a concave spherical shape to capture the ball end.

19. The stabilizer system of claim 12 further comprising a first link body having a spherical proximal face adapted to interface with the articulating links and having a distal hub aligning and retaining the cylindrical sleeve when the tension cable is under tension.

20. The stabilizer system of claim 12 wherein the cylindrical sleeve has a proximal end surface having a spherical shape to interface with the articulating links.

* * * * *